United States Patent
Landi

Patent Number: 5,141,522
Date of Patent: Aug. 25, 1992

[54] COMPOSITE MATERIAL HAVING ABSORBABLE AND NON-ABSORBABLE COMPONENTS FOR USE WITH MAMMALIAN TISSUE

[75] Inventor: Henry P. Landi, Westchester, N.Y.

[73] Assignee: American Cyanamid Company, Stamford, Conn.

[21] Appl. No.: 823,619

[22] Filed: Jan. 21, 1992

Related U.S. Application Data

[63] Continuation of Ser. No. 475,564, Feb. 6, 1990, abandoned.

[51] Int. Cl.⁵ .............................................. A61F 2/54
[52] U.S. Cl. ........................................ 623/66; 623/11; 623/13; 428/225; 606/154; 606/230
[58] Field of Search ................... 606/151, 154, 230; 623/11, 13, 66; 428/225

[56] References Cited

U.S. PATENT DOCUMENTS

| | | | |
|---|---|---|---|
| 3,272,204 | 9/1966 | Artandi et al. | 623/1 |
| 3,407,096 | 10/1968 | Landi . | |
| 3,407,249 | 10/1968 | Landi . | |
| 3,527,616 | 9/1970 | Landi . | |
| 4,052,988 | 10/1977 | Dotti et al. . | |
| 4,286,341 | 9/1981 | Greer et al. | 623/1 |
| 4,416,028 | 11/1983 | Eriksson et al. | 623/1 |
| 4,610,688 | 9/1986 | Silvestrini et al. | 623/1 |
| 4,759,765 | 7/1988 | Van Campen | 623/13 |
| 4,849,285 | 7/1989 | Dillon | 623/13 |
| 5,092,884 | 3/1992 | Devereux et al. | 623/11 |

OTHER PUBLICATIONS

"Fluorocarbons Available in New Configurations", Materials in Design Engineering, May 1965, pp. 5-7.
Abstract of Japanese Patent No. 62152467-A published Jul. 7, 1987.
Abstract of European Patent No. 256,748-A published Feb. 24, 1988.
Abstract of U.S. Pat. No. 4,643,734 patented Feb. 17, 1987.
Abstract of Oral Presentation by Errede et al. "Microporous Reactive Membranes" given Jul. 17, 1987.
"E. M. Technology", 3M Corporation, circa 1984.
"Soft Tissue Patch", W. L. Gore and Associates, 1984.

Primary Examiner—Randall L. Green
Assistant Examiner—Paul Prebilic
Attorney, Agent, or Firm—Charles F. Costello, Jr.

[57] ABSTRACT

The invention is a composite material of two or more biocompatible polymers, at least one of which is polytetrafluoroethylene (PTFE) and one of which is a bioabsorbable polymer. The nonabsorbable PTFE is used in the composite as a reinforcing binder. The reinforcing binder is a network of unsintered, interconnected micro-fibers which are formed, for example, by blending with a thermoplastic polymer vehicle, such as polymethylmethacrylate which is subsequently extracted. The bioabsorbable component is contained within the structure of the PTFE microfibrils. This composite is useful in the repair of mammalian tissue where tissue ingrowth and permenant support is required.

20 Claims, No Drawings

5,141,522

COMPOSITE MATERIAL HAVING ABSORBABLE AND NON-ABSORBABLE COMPONENTS FOR USE WITH MAMMALIAN TISSUE

This is a continuation of co-pending application Ser. No. 07/475,564, filed on Feb. 6, 1990, now abandoned.

BACKGROUND AND SUMMARY OF THE INVENTION

This invention relates to a composite of two or more biocompatible polymers, at least one of which is polytetrafluoroethylene (PTFE) and the other component being a bioabsorbable polymer. The nonabsorbable PTFE is used in the composite as a reinforcing binder. The reinforcing binder is a network of unsintered, interconnected microfibers. The microfibers can be formed, for example, by blending with a thermoplastic polymer vehicle, such as polymethylmethacrylate. The bioabsorbable polymer component can be present in the form of a particulate filler contained within the PTFE microfibrillar structure. The bioabsorbable particulate component can be micropulverized and could be, for example, polyglycolic acid (PGA), polylactic acid (PLA), a homo- or copolymer of trimethylene carbonate (TMC), and blends of the same or similar polymers. The polymethylmethacrylate is subsequently extracted with a suitable solvent. The resulting microporous structure has a tortuous porosity.

Alternatively, the bioabsorbable polymer can serve as the thermoplastic vehicle during the PTFE fibrillation process thus resulting in a nonporous reinforced composite structure. The bioabsorbable polymer vehicle component could be a copolymer of polyglycolic acid and trimethylene carbonate (GLY/TMC) or other bioabsorbable thermoplastic.

The composite described in this application may be useful in many biomedical applications, such as a tissue, hernia, or ligament repair device, a burn or wound dressing, a pledget, a drug delivery system and a tubular article, for example a vascular graft. The bioabsorbable component enhances tissue ingrowth within the fibrillar PTFE matrix. The nonabsorbable microfibrillar PTFE matrix provides additional support, direction and strength to the natural tissue formation.

The composite polymer structure described in this invention is useful in biomedical applications, such as in tissue repair, hernia repair, ligament repair, burn and wound dressing, pledgets, drug delivery systems, vascular grafts, etc. The bioabsorbable component enhances tissue ingrowth within the fibrillar PTFE matrix, which provides additional support, direction and strength to the natural tissue formation.

An advantage of this invention is that since a thermoplastic vehicle is used to form the fibrillar PTFE matrix, it therefore can be extruded into many different shapes such as a rod, tube, tape, film, or other intricate forms before extracting the thermoplastic.

Another advantage is that the PTFE is unsintered. Thus, the break down temperature of known bioabsorbable polymers (e.g., less than about 250° C.) is avoided in the processing of the composite of this invention.

The completely fibrillated, unsintered polytetrofluoroethylene (PTFE) reinforcing binder of this invention has advantages over a prior art porous, sintered PTFE product. For a disclosure of a sintered PTFE product, see, e.g., "Fluorocarbons Available in New Fibrous, Porous Configurations" published in Materials In Design Engineering, pages 5–7, May, 1965, which is incorporated herewith by reference.

Some of the advantages of this invention, in summary form, are as follows. A filler can be added directly to the PTFE polymer without subjecting it to the detrimental effects of the sintering temperature (approximately 325° F.) of PTFE. Also, a level as high as 97% filler content in the unsintered PTFE polymer can be achieved.

The prior art describes methods of preparation and nonbiological uses of fibrillar PTFE. The nonbiological uses include electrochemical applications. See, e.g., U.S. Pat. Nos. 3,527,616; 3,407,249; and 3,407,096 which are incorporated herein by reference.

A composite material for use with mammalian tissue has been invented. The composite material comprises:

a) an unsintered, microfibrillar, nonabsorbable biocompatible component prepared from polytetrafluoroethylene, and from a polymer prepared from one or more monomers selected from the group consisting of lactides, carbonates, oxalates and lactones, and optionally c) a nonabsorbable, biocompatible thermoplastic component manufactured from a polymer which is liquid at a temperature from about 150° to 200° C. and solid at ambient temperature, and which provides additional integrity to the unsintered component. In one embodiment, the bioabsorbable component is selected from the group consisting of lactides, carbonates and lactones. In a specific embodiment, the lactides are selected from the group consisting of glycolide and 3,6-dimethyl-1,4-dioxane-2,5-dione; the carbonate is 1,3-dioxan-2-one; and the lactones are selected from the group consisting of e-caprolactone and 1,4-dioxan-2-one. In another embodiment, the bioabsorbable component is manufactured from glycolide.

In combination with any of the above embodiments, other embodiments are the bioabsorbable component enmeshed in the pores of the unsintered component; the composite material in the form of a sheet or a hollow tube; and the nonabsorbable, thermoplastic component being poly(ethylenevinylacetate).

Still another embodiment is wherein the nonabsorbbable, thermoplastic component is enmeshed in the pores of the unsintered component. In a specific embodiment, the nonabsorbable, thermoplastic component is poly(ethylenevinyl acetate).

An alternative composite material for use with mammalian tissue has also been invented. The alternative composite material comprises:

a) an unsintered, microfibrillar, non-absorbable biocompatible component prepared from polytetrafluoroethylene, and b) a particulate bioabsorbable component manufactured from a polymer prepared from one or more monomers selected from the group consisting of lactides, carbonates, oxalates and lactones, and optionally c) a non-absorbable, biocompatible thermoplastic component manufactured from a polymer which is liquid at a temperature from about 150° to 200° C. and solid at ambient temperature, and which provides additional integrity to the unsintered component. In one embodiment, the particulate bioabsorbable component is selected from the group consisting of lactides, carbonates and lactones. In a specific embodiment, the lactides are selected from the group of glycolide and 3,6-dimethyl-1,4-dioxan-2,5-dione; the carbonate is 1,3-dioxan-2-one; and the lactones are selected from the group consisting of e-caprolactone and 1,4-dioxan-2-one. In another embodiment, the bioabsorbable component is manufactured from glycolide.

In combination with any of the above embodiments, other embodiments are the particulate bioabsorbable component being micropulverized; the composite material in the form of a sheet or a hollow tube; and the nonabsorbable, thermoplastic component being poly(ethylene-vinyl acetate).

Another alternative composite material for use with mammalian tissue has also been invented. The other alternative composite material comprises a first part consisting of the two component and optional three component composite material described above; and a second part affixed to at least one side of the first part. The second part comprises a bioabsorbable textile reinforcement component. The bioabsorbable reinforcement component is woven or knitted, and is manufactured from the same or a different polymer than the bioabsorbable component of the first part. In one embodiment, the bioabsorbable textile reinforcement component is selected from the group consisting of lactides, carbonates and lactones. In a specific embodiment, the lactides are selected from the group consisting of glycolide and 3,6-dimethyl-1,4-dioxan-2,5-dione; the carbonate is 3-dioxan-2-one; and the lactones are selected from the group consisting of e-caprolactone and 1,4-dioxan-2-one. In another embodiment, the textile reinforcement material is affixed to both sides of the first part. In a specific embodiment, the reinforcement material is laminated to the first part.

A drawing which describes the shape and/or geometrical configuration of the composite material is not necessary for an understanding of this invention. That is, any person skilled in the composite art will know how to manufacture and how to use the invention by reading this specification generally, and the examples specifically.

DESCRIPTION OF THE PREFERRED EMBODIMENT(S)

The material contains a fibrillated form of polytetrafluoroethylene (PTFE). It is processed without fusing the polymer at its sintering temperature (about 327° C.). It is a porous, membrane-like structure which is formed by mixing micro-particles of PTFE with a molten thermoplastic polymer, such as polymethylmethacrylate. The thermoplastic blend is then formed into a film, or other configuration, and the thermoplastic phase is subsequently extracted with a suitable solvent. The resultant pliable unsintered, fibrillar PTFE has a tortuous porous structure and is an excellent binder for many functional fillers.

One or more bioabsorbable polymers PGA fibers and/or micropulverized PGA powder can be incorporated into this porous PTFE fibrillar matrix. This bioabsorbable filler could enhance tissue ingrowth within its inherent tortuous porous structure. Therefore, it would be useful in ligament replacement and repair, membrane organ separators, burn or wound dressings, hernia repair, pericardial substitute etc.

Some changes could be made in the preparation of the film to reduce the fabricating temperatures below 100° C. This might include the use of extractable polymers or other extractable vehicles other than polymethylmethacrylate. Also, the coagulation of the PTFE dispersion as described in an article entitled, "Extrusion Properties of Lubricated Resin From Coagulated Dispersion," (Industrial and Engineering Chemistry, Vol. 44, No. 8, August 1952, p. 1805) results in a viscous mass which might be milled and fabricated to form a completely fibrous PTFE sheet similar to those prepared by the present process. Other improvements in the process might include the use of water soluble polymers such as polyethylene oxide.

Various fillers can be incorporated into this film to levels as high as 97%. As a filled, coated, or impregnated material, this unique porous, fibrous, unsintered PTFE offers a vast number of possibilities related to the combined properties of PTFE in this form with those of its filler, coating, etc. The use of additional extractable fillers to modify the structure has been demonstrated (i.e. the postextraction of colloidal silica from catalyzed carbon filled electrode structures) as disclosed in U.S. Pat. No. 3,527,616, which is incorporated herein by reference.

The fibrillar PTFE composite may be modified by combination with other reinforcing agents, such as meshes, woven fabrics, knitted fabrics, etc. prepared from biocompatible polymers. Also, the PTFE (in the micropulverized or dispersion form before fibrillating) can be incorporated directly into a bioabsorbable thermoplastic polymer, such as a homopolymer of polyglycolic acid (PGA), or a copolymer of PGA, e.g. one containing glycolic acid ester and trimethylene carbonate linkages (GLY/TMC), thus forming the microfibrillar structure in situ and eliminating the extractable thermoplastic vehicle. The fibrillar PTFE reinforced bioabsorbable polymer may also be extruded as a fiber for use as a suture, woven fabric, etc.

The thermoplastic vehicle may be removed such as by extraction with a suitable solvent. The remaining unsintered, fibrillar PTFE has a tortuous, microporous structure which is an excellent binder at levels as low as 1% for many functional fillers including bioabsorbable materials such as PGA, GLY/TMC and polydioxanone. The novel feature of this invention is the addition of a bioabsorbable filler which enhances tissue ingrowth within the tortuous, microporous fibrillar structure of the non-absorbable PTFE, which acts as reinforcement for the new tissue growth.

This fibrous, unsintered PTFE may be used as a carrier, reinforcing agent, or binder for other polymeric materials, both thermoplastic or thermoset, incorporated directly or by post-impregnation to further enhance the composite structure and degree of porosity (from non-porous to highly porous).

As used in the examples below, the term Acrylite and Acrylite H-12 are trademarks of American Cyanamide Company, N.J., U.S. for polymer compounds, such as a polymethylmethacrylate (herein abbreviated PMMA) compound. Also as used in the examples below, the term 30B susp. may be a condensation of the term Teflon ™ 30B suspension, which term may be a trademark of E.I. duPont & Co., De., U.S. for polytetrafluoroethylene in an aqueous suspension.

EXAMPLES 1 TO 5

The Examples 1 and 4 to 7, respectively, of U.S. Pat. No. 3,407,249 issued Oct. 22, 1968 to H. Landi and entitled "Porous, Extensively Fibrillated Polytetrafluoroethylene and Method of Preparing Same" are incorporated here by reference.

EXAMPLE 6

The Example 1 of U.S. Pat. No. 3,527,616 issued Sep. 8, 1970 to H. Landi and entitled "Electrodes for Free Electrolyte Fuel Cells" is incorporated here by reference.

EXAMPLE 7

The Example 1 of U.S. Pat. No. 3,407,096 issued Oct. 22, 1968 to H. Landi and entitled "Fuel Cell and Method for Preparing the Electrodes" is incorporated herein by reference.

EXAMPLE 8

A microporous bicomponent composite structure of fibrillated PTFE semi-permeable membrane sheet containing high levels of micropulverized PGA polymer is prepared as follows:

On a rubber mill are heated to about 160°-170° C. a molten blend of the following ingredients, listed in order of addition, is mixed thoroughly:

| Blend No. | Components | Wt. q. |
|---|---|---|
| 1 | Acrylite TM H-12 Compound | 200 |
|   | 33.2 ml of PTFE In aqueous suspension - duPont 30B | 30 PTFE |
|   | PGA micropulverized to about 150 microns | 170 |

The micropulverized PGA powder is formed by grinding the polymer pellets in a Fitzpatrick Mill mixed with dry ice to prevent overheating. The resultant ground powder is sieved through a 100 mesh screen to recover the micropulverized powder of about 150 microns or less.

The blend was removed from the rubber mill in one uniform sheet. While the blended sheet was still hot from the mill, it was cut into 8 pieces of approximately equal size to be used for compressing into thinner sheets of film.

A disc was compressed from one of the pieces of Blend #1 between stainless steel caul plates and shim stock of 24 mils (0.024 inch) thick for ~15 min. at 350° F.-360° F. at a pressure of 30 tons on a 6 inch diameter ram. The platens of the molding press measured 12 inches × 12 inches in size.

The molded disc was removed from between the heated platens and cooled in another press under pressure for about 5 min.

The resultant disc of blended material measured approximately 10 inches in diameter, 24 mils (0.024 inch) thick, and weighed approximately 50 g.

The disc was subsequently immersed in acetone solvent to extract the PMMA (Acrylite TM polymer) phase. The resultant composite film structure is microporous and contains the remaining unextractable polymers, that is, PGA (85 wt. %) and fibrillated PTFE (15 wt. %) binder.

EXAMPLE 9

The following tricomponent blend is prepared similarly to Example 8.

A microporous fibrillated PTFE containing PEVA and high levels of micropulverized PGA polymer is blended on a rubber mill pre-heated to ~160-170° C. The composition of the blend is as follows:

| Blend No. | Components | Wt. q. |
|---|---|---|
| 2 | Acrylite TM H-12 Compound | 200 |
|   | PTFE (DuPont 30B susp.) | 30 |
|   | Poly(ethylene-Vinyl Acetate). (PEVA) | 30 |
|   | PGA (micropulv.) | 140 |

The blend was removed from the rubber mill in one uniform sheet. While the blended sheet was still hot from the mill, it was cut into 8 approximately equal parts to be used for pressing into thinner sheets of film.

A disc was compressed from one of the pieces of Blend #2 between Stainless Steel (SS) caul plates and shim stock of 24 mils. thick. A disc was formed which measured approximately 10.5" diameter and 24 mils thick (0.024") and weighed 49 g.

After extracting the PMMA (Acrylite TM) polymer phase with solvent, the resultant microporous film structure is a composite of the remaining unextractable polymer components namely, PGA (70 wt. %), PEVA (15 wt. %), and fibrillar PTFE (15%).

EXAMPLE 10

A micropulverized PGA polymer biocomponent blend, Example 9, is blended on a rubber mill pre-heated ~160°-70° C. The composition of the blend is as follows:

| Blend No. | Components | Wt. q. |
|---|---|---|
| 3 | Acrylite TM H-12 Compound | 200 |
|   | PTFE (30B susp.) | 10 (12 ml.) |
|   | PGA (micropulv.) | 190 |

The blend was removed from the rubber mill in one uniform sheet. While the blended sheet was still hot from the mill, it was cut into 8 approximately equal parts to be used for pressing into thinner sheets of film.

One plaque from blend #3 above was compressed between stainless steel caul plates and shim stock (44 mil. or 0.044") for about 15 min. at 350-360° F. at a pressure of tons on a 6" diameter ram. The platens measured 12×12". They were removed and cooled under pressure for about 5 min. A disc was formed which measured approximately 7.5 inches diameter and approximately 43 mils thick (0.043") weighing 52 g.

After extruding the PMMA (Acrylite TM) polymer phase with solvent, the resultant microporous film structure is a PGA (95 wt. %), and fibrillar PTFE (5 wt %).

EXAMPLE 11

The density of sheets compressed to a thickness of mils (0.024") from the blends in Examples 8 to 10 are as follows:

| Example 8 | Sheet #1 | 1.28 g/cc |
|---|---|---|
|   | Sheet #2 | 1.33 g/cc |
| Example 9 | Sheet #1 | 1.26 g/cc |
|   | Sheet #2 | 1.26 g/cc |
| Example 10 | Sheet #1 | 1.32 g/cc |
|   | Sheet #2 | 1.32 g/cc |

The above sheets were extracted by immersing them four times in acetone, at 16 hours each, replacing the acetone after each 16 hour immersion with clean fresh acetone. The sheets were then washed in methanol, pressed between blotter paper, and air dried.

EXAMPLE 12

The following is the PMMA extraction data for the sheets of Examples 8 to 10.

|  |  | Weight After Acetone Extraction | Weight Before Acetone Extraction | % PMMA Extracted |
|---|---|---|---|---|
| Example 8: | #1 | 30.34 g. | 61.82 g. | 49.07 |
|  | #2 | 21.71 g. | 43.01 g. | 50.47 |
| Example 9: | #1 | 23.32 g. | 47.2 g. | 49.4 |
|  | #2 | 23.68 g. | 47.9 g. | 49.44 |
| Example 10: | #1 | 25.99 g. | 53.2 g. | 48.9 |
|  | #2 | 27.67 g. | 56.4 g. | 49.06 |

EXAMPLE 13

Sheets #2 from Example above were cut into pieces measuring ½ inch ×1 inch and were sterilized with ethylene oxide gas in preparation for animal implant testing.

Samples of these three types of microporous composite membrane structures were evaluated for material integrity, adsorption, and tissue reaction when implanted subcutaneously in rabbits for up to 6 months.

Two samples of each membrane were implanted subcutaneously on each side of the abdominal midline in each of five adult New Zealand albino rabbits. Test intervals were scheduled for 14 days, 1, 2, 3 and 6 months. The rabbit scheduled for six months received only one of the Example 11 samples.

At the end of the test interval one sample from each membrane composition was resected en bloc and prepared for microscopic examination. The other sample was removed and subjected to manual manipulation to determine its consistency.

Results

Morbidity and Mortality

Four of the animals were healthy at term. One animal developed ulcerated foot and heel pads and was sacrificed at 65 days instead of the scheduled 3 months. This problem was not associated with the implant materials.

Summary and Conclusions

Initially, all three membrane types were pliable and resistant to stretch. By 14 days and thereafter the bicomponent materials were pliable but "taffy" like. The tricomponent membrane maintained its integrity throughout the study. No adverse gross tissue response nor gross evidence of absorption was seen at any interval.

Microscopically the membranes stimulated a slight to moderate phagocytic response and thin fibrous capsule formation. The least response was seen with the tricomponent membrane. Material degradation appears to be due more to phagocytosis than to hydrolysis.

Due to the material integrity and lack of tissue reaction seen with the 15% PTFE/15% PEVA/70% PGA membranes, this material is preferred. Possible uses for the material are as a soft tissue patch and/or a segmental replacement of a hollow organ. This material, either alone or in combination with other absorbable (e.g., GLY/TMC) and/or nonabsorbable (e.g., a polybutester) materials, may also be useful to prevent or reduce tissue adhesions and/or as a pericardial patch.

The gross observations are shown in Table 1.

TABLE 1

| | Tissue Reaction | | | | | Consistency | | | | |
|---|---|---|---|---|---|---|---|---|---|---|
| Sample ID | 14 Days | 30 Days | 59 Days | 65 Days | 184 Days | 14 Days | 30 Days | 59 Days | 65 Days | 184 Days |
| Example 9 | none | none | none | none | none | stretchy "taffy-like" pliable | same | same | same | same |
| Example 10 | none | none | none | none | none | no stretch pliable strong | same | same | same | same |
| Example 11 | none | slight neovascularity | none | none | none | no stretch pliable fibrous on breaking | stretchy pliable | stretchy "taffy-like" weak | very "taffy-like" | same |

I claim:

1. A composite material for use with mammalian tissue consisting essentially of:
   (a) an unsintered, microfibrillar, non-absorbable biocompatible component prepared from polytetrafluoroethylene,
   (b) a particulate bioabsorbale filler manufactured from a polymer prepared from one or more monomers selected from the group consisting of lactides, carbonates, oxalates and lactones, and
   (c) a non-absorbable, biocompatible thermoplastic component manufactured from a polymer which is liquid at a temperature from about 150° to 200° C. and solid at ambient temperature, and which provides additional integrity to the unsintered component.

2. The material of claim 1 wherein the particulate bioabsorbable filler is selected from the group consisting of lactides, carbonates and lactones.

3. The material of claim 2 wherein the lactides are selected from the group consisting of glycolide and 3,6-dimethyl-1,4-dioxan-2,5-dione; the carbonate is 1,3-dioxan-2-one; and the lactones are selected from the group consisting of e-caprolactone and 1,4-dioxan-2-one.

4. The material of claim 3 wherein the particulates, bioabsorbable filler is manufactured from glycolide.

5. A composite material for use with mammalian tissue comprising a first part consisting of the composite material of claim 1 in the form of a sheet, the sheet having two sides; and a second part affixed to at least one side of said sheet, the second part comprising a bioabsorbable textile reinforcement component, the bioabsorbable reinforcement component being woven or knitted, and manufactured from the same or a different polymer then the particulate bioabsorable filler of the first part.

6. The material of claim 5 wherein the bioabsorable textile reinforcement component is selected from the group consisting of lactides, carbonates and lactones.

7. The material of claim 6 wherein the lactides are selected from the group consisting of glycolide and 3,6-dimethyl-1,4-dioxan-2,5-dione; the carbonate is 1,3-dioxan-2-one; and the lactones are selected from the group consisting of e-caprolactone and 1,4-dioxan-2-one.

8. The material of claim 7 wherein said bioabsorable textile reinforcement material is affixed to both sides of the first part.

9. The material of claim 8 wherein said bioabsorable textile reinforcement component is laminated to said first part.

10. The material of claims 1 or 2 or 3 or 4 wherein the non-absorbable, thermoplastic component is poly(ethylene-vinyl acetate).

11. A composite material for use with mammalian tissue consisting essentially of:
(a) an unsintered, microfibrillar, non-absorbable biocompatible component prepared from polytetrafluoroethylene,
(b) a micropulverized bioabsorbable powder manufactured from a polymer prepared from one or more monomers selected from the group consisting of lactides, carbonates, oxalates and lactones, and
(c) a non-absorbable, biocompatible thermoplastic component manufactured from a polymer which is liquid at a temperature from about 150° to 200° C. and solid at ambient temperature, and which provides additional integrity to the unsintered component.

12. A composite material for use with mammalian tissue consisting essentially of:
(a) an unsintered, microfibrillar, non-absorbable biocompatible component prepared from polytetrafluoroethylene, and
(b) a bioabsorbable powder manufactured from a polymer prepared from one or more monomers selected from the group consisting of lactides, carbonates, oxalates and lactones, and optionally
(c) a non-absorbable, biocompatible thermoplastic component manufactured from a polymer which is liquid at a temperature from about 150° to 200° C. and solid at ambient temperatures. and which provides additional integrity to the unsintered component.

13. The material of claim 11 wherein the composite material is in the form of a sheet.

14. The material of claim 11 wherein the composite material is in the form of a hollow tube.

15. The material of claim 7 wherein the non-absorbable thermoplastic component is poly(ethylene-vinyl acetate).

16. The material of claim 13 wherein said non-absorbable, thermoplastic component is poly(ethylene-vinyl acetate).

17. A composite material for use with mammalian tissue comprising a first part consisting of the composite material of claims 11 or 12 in the form of a sheet, the sheet having two sides; and a second part affixed to at least one side of said sheet, the second part comprising a bioabsorbable textile reinforcement component, the bioabsorbable textile reinforcement component being woven or knitted, and manufactured from the same or a different polymer than the bioabsorbable powder of the first part.

18. The material of claim 17 wherein the bioabsorable powder and textile reinforcement component are selected from the group consisting of lactides, carbonates and lactones.

19. The material of claim 18 wherein the lactides are selected from the group consisting of glycolide and 3,6-dimethyl-1,4-dioxan-2,5-dione; the carbonate is 1,3-dioxan-2-one; and the lactones are selected from the group consisting of ϵ-caprolactone and 1,4-dioxane-2-one.

20. The material of claim 18 wherein the textile reinforcement component is affixed to both sides of the first part.

* * * * *